United States Patent
Takeno et al.

(10) Patent No.: US 10,213,100 B2
(45) Date of Patent: Feb. 26, 2019

(54) OPTICAL COHERENCE TOMOGRAPHY APPARATUS AND DATA PROCESSING PROGRAM

(71) Applicant: NIDEK CO., LTD., Gamagori, Aichi (JP)

(72) Inventors: Naoki Takeno, Aichi (JP); Yasuhiro Furuuchi, Aichi (JP); Hajime Namiki, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 692 days.

(21) Appl. No.: 14/753,274

(22) Filed: Jun. 29, 2015

(65) Prior Publication Data
US 2015/0374227 A1 Dec. 31, 2015

(30) Foreign Application Priority Data

Jun. 30, 2014 (JP) ................................ 2014-135450
Dec. 11, 2014 (JP) ................................ 2014-251348

(51) Int. Cl.
*A61B 3/10* (2006.01)
*A61B 5/02* (2006.01)
(Continued)

(52) U.S. Cl.
CPC ............ *A61B 3/102* (2013.01); *A61B 5/0066* (2013.01); *A61B 5/02* (2013.01); *A61B 5/7275* (2013.01);
(Continued)

(58) Field of Classification Search
CPC ........... A61B 3/14; A61B 3/0025; A61B 3/12; A61B 3/102; A61B 3/113; A61B 3/33;
(Continued)

(56) References Cited

U.S. PATENT DOCUMENTS

| 2008/0025570 A1* | 1/2008 | Fingler ................. A61B 3/102 382/107 |
| 2012/0120408 A1 | 5/2012 | Yasuno et al. |
| 2013/0176532 A1* | 7/2013 | Sharma ................. A61B 3/102 351/206 |
| 2013/0301008 A1* | 11/2013 | Srivastava ......... G01B 9/02083 351/246 |

FOREIGN PATENT DOCUMENTS

WO 2010/143601 A1 12/2010

OTHER PUBLICATIONS

Hansford C. Hendargo et al., "Automated non-rigid registration and mosaicing for robust imaging of distinct retinal capillary beds using speckle variance optical coherence tomography", Biomedical Optics Express, vol. 4, No. 6, Jun. 1, 2013, 19 pgs. total.
(Continued)

*Primary Examiner* — Elmer M Chao
(74) *Attorney, Agent, or Firm* — Sughrue Mion, PLLC

(57) ABSTRACT

An optical coherence tomography apparatus includes an OCT optical system configured to detect an OCT signal based on measurement light scanned on scan positions of a subject including a blood vessel network by a scanning unit and reference light. The optical coherence tomography apparatus is configured to execute: a signal processing instruction of processing OCT signals which are temporally different from each other with respect to a same position on the subject and generating a motion contrast image which images distribution of a moving object in a depth direction at each of the scan positions based on the OCT signals; and a detecting instruction of analyzing a profile in the depth direction of the motion contrast image generated by the signal processing unit and detecting a change resulting from the blood vessel to detect the blood vessel network included in the subject.

14 Claims, 11 Drawing Sheets

(51) Int. Cl.
  *A61B 5/00* (2006.01)
  *G01N 21/47* (2006.01)
  *A61B 5/026* (2006.01)
  *A61B 3/00* (2006.01)
  *A61B 3/14* (2006.01)
  *A61B 3/113* (2006.01)

(52) U.S. Cl.
  CPC ........... *A61B 3/0025* (2013.01); *A61B 3/0033* (2013.01); *A61B 3/113* (2013.01); *A61B 3/145* (2013.01); *A61B 5/0059* (2013.01); *A61B 5/0261* (2013.01); *G01N 21/4795* (2013.01)

(58) Field of Classification Search
  CPC .. A61B 3/145; A61B 5/59; A61B 5/66; A61B 5/0261; A61B 5/7275; G01N 21/4795
  See application file for complete search history.

(56) References Cited

OTHER PUBLICATIONS

Yonghua Zhao et al., "Phase-resolved optical coherence tomography and optical Doppler tomography for imaging blood flow in human skin with fast scanning speed and high velocity sensitivity", Optics Letters, vol. 25, No. 2, Jan. 15, 2000, 3 pgs. total.

Adrian Mariampillai et al., "Speckle variance detection of microvasculature using swept-source optical coherence tomography", Optics Letters, vol. 33, No. 13, Jul. 1, 2008, 3 pgs.

Vivek J. Srinivasan et al., "Rapid volumetric angiography of cortical microvasculature with optical coherence tomography", Optics Letters, vol. 35, No. 1, Jan. 1, 2010, 3 pgs.

* cited by examiner

*FIG.9A*          *FIG.9B*
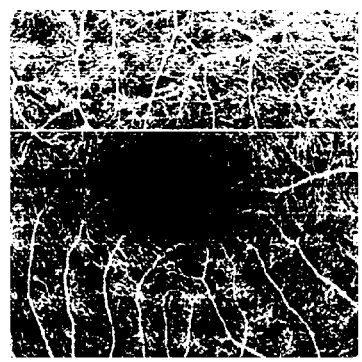 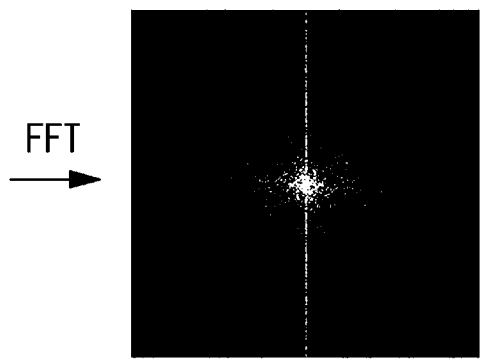
*FIG.9C*
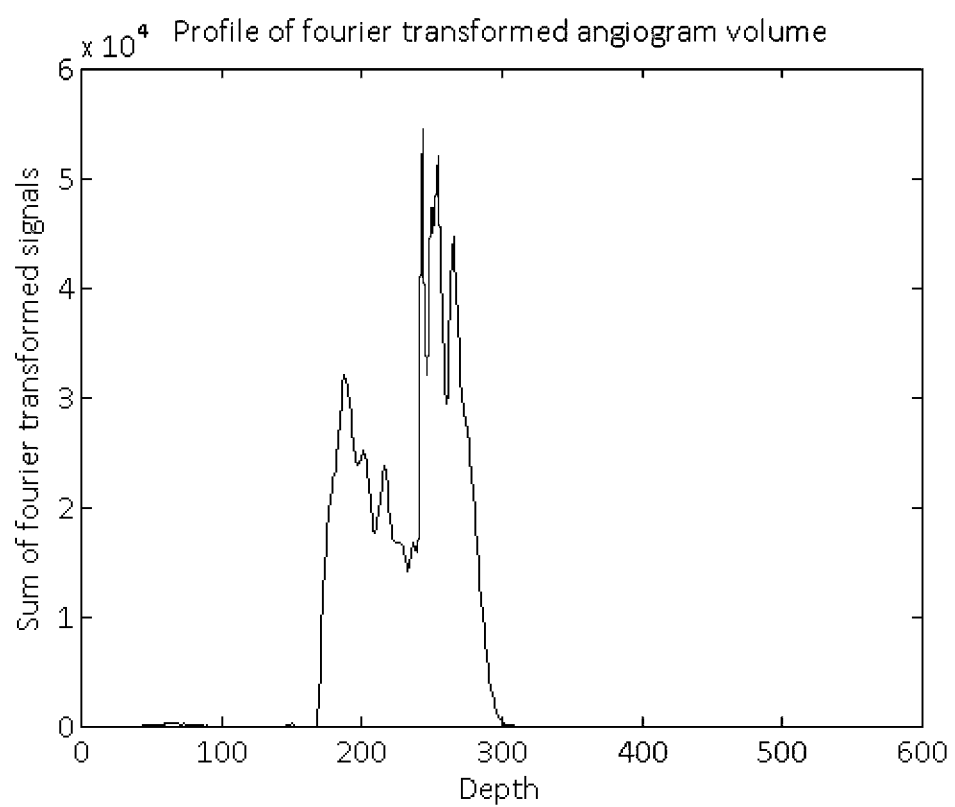

OPTICAL COHERENCE TOMOGRAPHY APPARATUS AND DATA PROCESSING PROGRAM

CROSS REFERENCE TO RELATED APPLICATIONS

This application is based upon and claims the benefit of priorities of Japanese Patent Application No. 2014-135450 filed on Jun. 30, 2014 and Japanese Patent Application No. 2014-251348 filed on Dec. 11, 2014, the contents of which are incorporated herein by reference in its entirety.

BACKGROUND

The present disclosure relates to an optical coherence tomography apparatus which obtains motion contrast data of a subject, and a data processing program.

In the related art, as an apparatus which performs angiography, for example, a fundus camera, a scanning laser optometry apparatus, or the like has been known. In this case, a contrast agent which emits light with excitation light is injected into a body. The apparatus receives light from the contrast agent to obtain an angiogram. That is, in the related art, the injection of the contrast agent is required.

RELATED ARTS

International Publication No. 2010/143601
H. C. Hendargo et al. Biomed. Opt. Express, Vol. 4, No. 6, p. 803/May 2013
Yonghua Zhao et al. OPTICS LETTERS/Vol. 25, No. 2/Jan. 15, 2000
Adrian Mariampillai et al. OPTICS LETTERS/Vol. 33, No. 13/Jul. 1, 2008
Vivek J. Srinivasan et al. OPTICS LETTERS/Vol. 35, No. 1/Jan. 1, 2010

SUMMARY

In recent years, an apparatus which obtains a motion contrast image by applying an OCT technique without using a contrast agent has been suggested. In the present apparatus, an en-face (a surface perpendicular to a measurement optical axis by OCT) motion contrast image may be generated. In this case, for example, a retinal layer is separated into a retinal nerve fiber layer (NFL), a ganglion cell layer (GCL), an inner plexiform layer (IPL), and the like based on a luminance profile in a depth direction of an OCT image, and a region where it is estimated that a blood vessel is present anatomically is obtained based on the position of the separated retinal layer. An en-face motion contrast image is generated for each region where it is estimated that a blood vessel is present anatomically. That is, segmentation is performed using an OCT image which becomes a base for obtaining a motion contrast image.

However, a blood vessel may be present at a position, at which a blood vessel is not present normally, due to a disease or the like. In this case, even if an en-face image is generated for each region which is estimated anatomically, it may be difficult to generate a satisfactory motion contrast image.

The present disclosure provides an optical coherence tomography apparatus capable of appropriately acquiring blood vessel information of a subject and a recording medium storing a program in consideration of the above-described problems.

In order to solve the above-described problems, the present disclosure includes the following configuration.

(1) An optical coherence tomography apparatus comprising:
an OCT optical system configured to detect an OCT signal based on measurement light scanned on a plurality of scan positions of a subject including a blood vessel network by a scanning unit and reference light corresponding to the measurement light;
a processor; and
a memory storing a computer program, when executed by the processor, causing the optical coherence tomography apparatus to execute:
a signal processing instruction of processing a plurality of OCT signals which are temporally different from each other with respect to a same position on the subject and generating a motion contrast image which images distribution of a moving object in a depth direction for each of the scan positions based on the plurality of OCT signals; and
a detecting instruction of analyzing a profile in the depth direction of the motion contrast image generated by the signal processing unit and detecting a change resulting from a blood vessel of the blood vessel network to detect the blood vessel network included in the subject.

(2) The optical coherence tomography apparatus according to (1),
wherein the detecting instruction causes the optical coherence tomography apparatus to detect a change resulting from the blood vessels at different positions in the depth direction to detect a plurality of the blood vessel networks, and separate the blood vessel networks into each of the blood vessel networks in the depth direction based on the detection results.

(3) The optical coherence tomography apparatus according to (1), wherein
the subject is an eye, and
the OCT optical system detects the OCT signal based on measurement light scanned on the plurality of scan positions of the fundus of the eye.

(4) The optical coherence tomography apparatus according to (1),
wherein the detecting instruction causes the optical coherence tomography apparatus to analyze a luminance profile in the depth direction and detect a change in luminance resulting from the blood vessel to detect the blood vessel network included in the subject.

(5) The optical coherence tomography apparatus according to (1),
wherein the detecting instruction causes the optical coherence tomography apparatus to analyze a luminance profile of a spatial frequency spectrum in the depth direction and detects a change in luminance resulting from the blood vessel to detect a blood vessel network included in the subject, the spatial frequency spectrum being obtained by two-dimensional Fourier transform of the motion contrast image.

(6) The optical coherence tomography apparatus according to (1),
wherein the detecting instruction causes the optical coherence tomography apparatus to detect, as a boundary of the blood vessel network, a depth where the profile has an extreme value.

(7) The optical coherence tomography apparatus according to (1), wherein
the OCT optical system is configured to acquire the plurality of OCT signals at each scan position in a two-dimensional manner by two-dimensionally scanning the measurement light on the subject, the signal processing instruction causes the optical coherence tomography apparatus to generate three-dimensional motion contrast data as an aggregate of motion contrast images having different transverse positions based on the plurality of OCT signals acquired in the two-dimensional manner, and the detecting instruction causes the optical coherence tomography apparatus to detect the blood vessel network in each of the motion contrast images to two-dimensionally detect the blood vessel network in the three-dimensional motion contrast data.

(8) The optical coherence tomography apparatus according to (7), wherein the computer program when executed by the processor causes the optical coherence tomography apparatus to further execute:

an en-face image generation instruction of generating an en-face image obtained by visualizing the motion contrast images in a front direction based on the profile in the depth direction in the blood vessel network detected by the detecting instruction.

(9) The optical coherence tomography apparatus according to (8), wherein the detecting instruction causes the optical coherence tomography apparatus to detect a change resulting from the blood vessels at different positions in the depth direction by analyzing the profile to detect a plurality of the blood vessel networks included in the subject, and to separate the blood vessel networks in the depth direction based on the detection results of the change resulting from the blood vessels at different positions in the depth direction, and the en-face image generation instruction causes the optical coherence tomography apparatus to generate an en-face image corresponding to each of the blood vessel networks based on a profile in the depth direction in each of the blood vessel networks separated by the detecting instruction.

(10) The optical coherence tomography apparatus according to (7), wherein the detecting instruction causes the optical coherence tomography apparatus to divide the three-dimensional motion contrast data into a plurality of small regions with respect to the front direction, analyze the profile in the divided small regions, and detect the change resulting from the blood vessel in each of the small regions to detect a blood vessel network included in the subject.

(11) A non-transitory computer readable recording medium storing a data processing program, which is executed by a processor of an optical coherence tomography apparatus including an OCT optical system configured to detect an OCT signal based on measurement light scanned on a plurality of scan positions of a subject including a blood vessel network by a scanning unit and reference light corresponding to the measurement light, the data processing program when executed by the processor of the optical coherence tomography apparatus causing the optical coherence tomography apparatus to execute:

a signal processing instruction of processing a plurality of OCT signals which are temporally different from each other with respect to a same position on the subject and generating a motion contrast image which images distribution of a moving object in a depth direction at each of the scan positions based on the plurality of OCT signals; and a detecting instruction of analyzing a profile in the depth direction of the motion contrast image generated by the signal processing unit and detecting a change resulting from the blood vessel to detect the blood vessel network included in the subject.

BRIEF DESCRIPTION OF THE DRAWINGS

FIGS. 9A to 9C are diagrams showing an example of a spatial frequency spectrum.

DESCRIPTION OF ILLUSTRATIVE EMBODIMENTS

<Outline>

Figure 1:
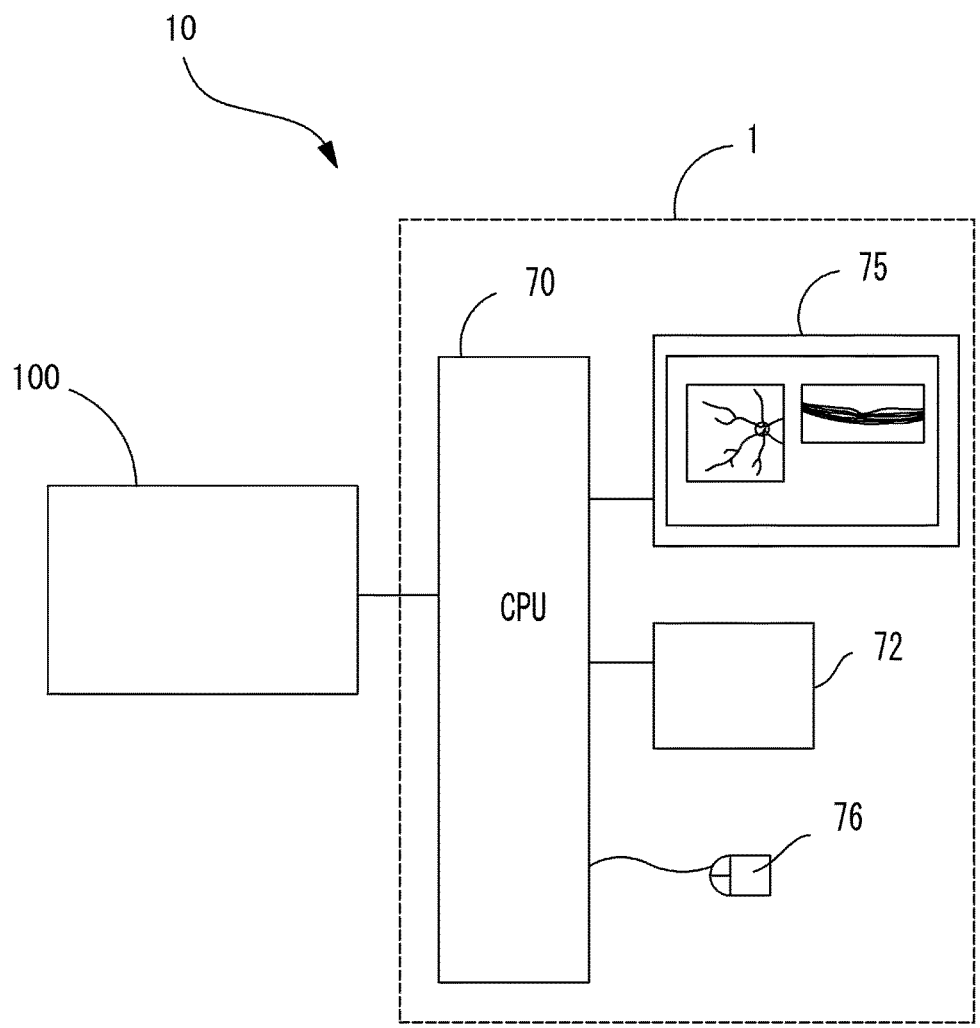
FIG. 1 is a block diagram illustrating the configuration of an optical coherence tomography apparatus.

Hereinafter, the outline of this example will be described referring to the drawings. An optical coherence tomography apparatus (see FIG. 1) of this example obtains a motion contrast image of a subject (for example, a subject's eye E; see FIG. 2). The subject may be, for example, a fundus Ef. An optical coherence tomography apparatus (hereinafter, abbreviated as the present apparatus) 10 primarily includes, for example, an OCT optical system 100 (see FIG. 1), a signal processing unit (for example, a control unit 70), and a blood vessel network detection unit (for example, the control unit 70).

The OCT optical system 100 detects, for example, an OCT signal by measurement light scanned on a subject including a blood vessel network by a scanning unit (for example, an optical scanner 108) and reference light corresponding to the measurement light.

The signal processing unit processes, for example, a plurality of OCT signals which are temporally different from each other with respect to the same position on the subject. Also, the signal processing unit generates, for example, a motion contrast image by imaging the distribution of a moving object in the depth direction at each scan position based on a plurality of OCT signals. If the motion contrast image is generated, a pseudo angiogram is acquired. In the following description, the motion contrast image may be described as a pseudo angiogram. The motion contrast image may be used to image a moving object in the depth direction at each scan position.

The blood vessel network detection unit analyzes, for example, a profile in the depth direction of the motion contrast image generated by the signal processing unit. Hereby, the blood vessel network detection unit detects a change resulting from a blood vessel to detect a blood vessel network included in the subject. A change resulting from a blood vessel may be, for example, a change resulting from the number of blood vessels, a change resulting from the presence or absence of a blood vessel, or a change resulting from the degree of unevenness in the depth direction. The blood vessel network detection unit may detect, for example, an edge position of a signal, a peak position of a signal, and a bottom position of a signal through signal processing in order to detect a change resulting from the blood vessel. In this way, the blood vessel network detection unit (image processing unit) may detect a change of a profile in the depth direction of the motion contrast image and may detect a blood vessel region based on the detection result. The blood vessel network detection unit may detect a characteristic portion resulting from the presence or absence of a blood vessel. For example, the blood vessel network detection unit may detect a position, at which a change of a signal resulting from a blood vessel is relatively smaller than other depth positions, as the boundary of the blood vessel network.

In the apparatus described above, a blood vessel network is detected directly from a motion contrast image, thereby facilitating imaging of the blood vessel network. It is also possible to cope with a case where a blood vessel appears in a layer in which a blood vessel is not present due to a disease.

The blood vessel network detection unit may analyze a profile in the depth direction of the motion contrast image and may detect a change resulting from each of blood vessels formed at different positions in the depth direction. Hereby, a plurality of blood vessel networks included in the subject may be detected. The blood vessel network detection unit may separate the blood vessel networks in the depth direction based on the detection results of the blood vessel networks.

The blood vessel network detection unit may include, for example, a region separation unit (for example, the control unit 70). For example, the region separation unit may analyze a profile in the depth direction of the motion contrast image and may detect a change resulting from each of blood vessels at different positions in the depth direction in the subject's eye E (for example, the fundus Ef or the like). Hereby, the region separation unit may detect a plurality of blood vessel networks included in the subject and may separate the blood vessel networks in the depth direction based on the detection results.

The blood vessel network detection unit may analyze a luminance profile (luminance distribution) in the depth direction and may detect a change in luminance resulting from a blood vessel to detect a blood vessel network included in the subject.

The blood vessel network detection unit may analyze a luminance profile in the depth direction of a spatial frequency spectrum when a motion contrast image is subjected to two-dimensional Fourier transform. The blood vessel network detection unit may detect a change in luminance resulting from a blood vessel of the luminance profile in the depth direction of the spatial frequency spectrum to detect a blood vessel network included in the subject.

The blood vessel network detection unit may detect, as the boundary of the blood vessel network, a depth where the profile in the depth direction of the motion contrast image has an extreme value.

The present apparatus 10 may further include an en-face image generation unit (for example, the control unit 70). For example, the en-face image generation unit may generate an en-face image obtained by visualizing the motion contrast image with respect to a front direction based on the profile in the depth direction in a blood vessel network detected by the blood vessel network detection unit. Hereby, it is possible to visualize a blood vessel network detected satisfactorily with respect to the front direction.

The blood vessel network detection unit may analyze a profile in the depth direction of the motion contrast image and may detect a change resulting from each of blood vessels formed at different positions in the depth direction. Hereby, the blood vessel network detection unit may detect a plurality of blood vessel networks included in the subject and may separate the blood vessel networks in the depth direction based on the detection results. In this case, the en-face image generation unit may generate an en-face image corresponding to each blood vessel network based on the profile in the depth direction in each blood vessel network separated by the blood vessel network detection unit.

Figure 6A:
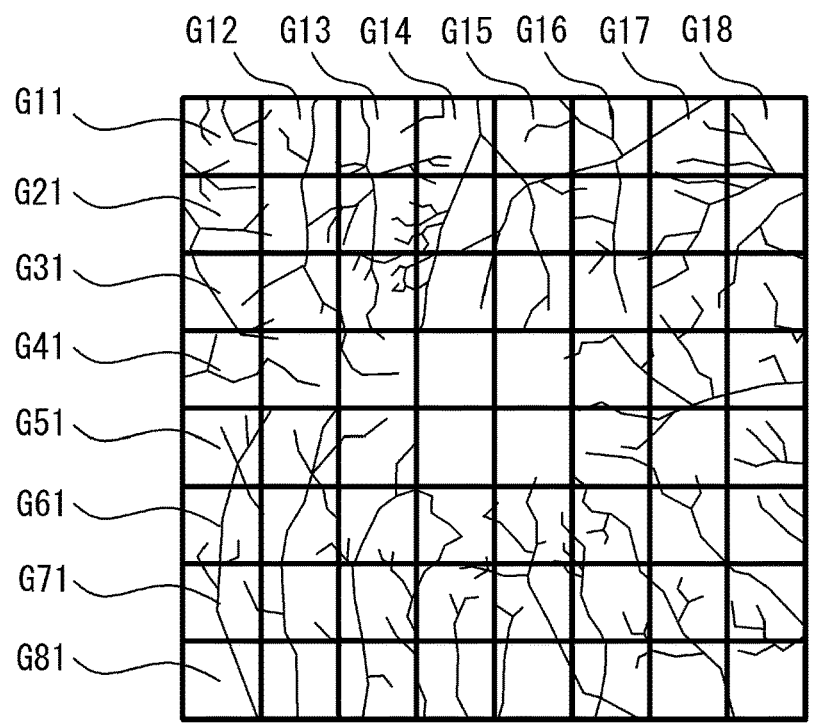
FIGS. 6A and 6B are image diagrams when a detection region of a blood vessel network is divided.
Figure 6B:
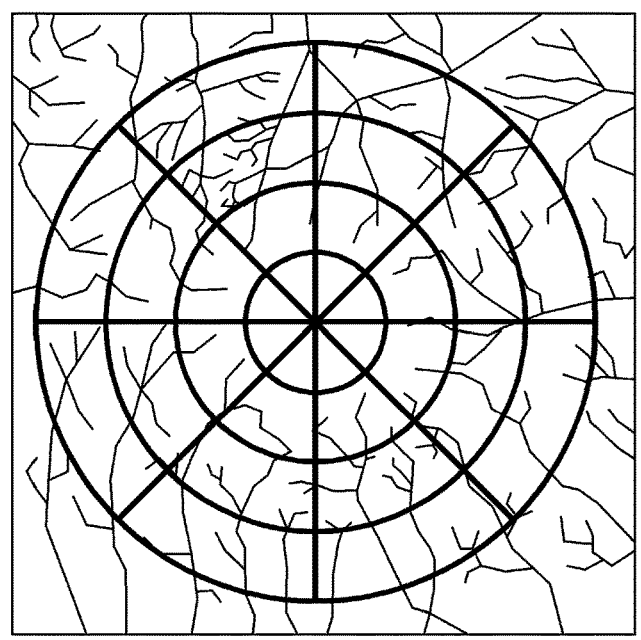

The blood vessel network detection unit may divide the three-dimensional motion contrast data into a plurality of small regions with respect to the front direction (see FIGS. 6A and 6B). The blood vessel network detection unit may analyze a profile in the divided small regions and may detect a change resulting from a blood vessel in each small region to detect a blood vessel network included in the subject. Hereby, for example, even if there is a place where a blood vessel cannot be detected, the blood vessel network detection unit can obtain a blood vessel network from nearby blood vessels.

The present apparatus 10 may be able to scan measurement light on the subject in a two-dimensional manner to acquire a plurality of OCT signals at each scan position in a two-dimensional manner. In this case, the signal processing unit may generate three-dimensional motion contrast data based on a plurality of OCT signals acquired in the two-dimensional manner. Three-dimensional motion contrast data is, for example, an aggregate of motion contrast images having different transverse positions. The blood vessel network detection unit may detect a blood vessel network in each motion contrast image to detect a blood vessel network in three-dimensional motion contrast data in a two-dimensional manner. Hereby, since it is possible to detect a blood vessel network with respect to the front direction (horizontal and vertical direction), it is possible to generate an en-face image in the detected blood vessel network.

A data processing program may be executed by a processor of the present apparatus 10. The data processing program may include, for example, a signal processing step and a blood vessel network detection step. The signal processing step may be, for example, a step in which a plurality of OCT signals which are temporally different from each other with respect to the same position on the subject are processed, and a motion contrast image obtained by imaging the distribution of a moving object in the depth direction at each scan position is generated based on a plurality of OCT signals. The blood vessel network detection step may be, for example, a step in which a profile in the depth direction of the motion contrast image generated in the signal processing step is analyzed and a change resulting from a blood vessel is detected to detect a blood vessel network included in the subject.

Example

Hereinafter, an exemplary example will be described referring to the drawings. FIG. 1 is a block diagram illustrating the configuration of an optical coherence tomography apparatus (hereinafter, also referred to as the present apparatus) 10 according to this example. As an example, the present apparatus 10 will be described as a fundus imaging apparatus which acquires a tomographic image of a fundus of a subject's eye.

An OCT device 1 processes a detection signal acquired by the OCT optical system 100. The OCT device 1 has the control unit 70. For example, the OCT optical system 100 images a tomographic image of the fundus Ef of the subject's eye E. For example, the OCT optical system 100 is connected to the control unit 70.

Figure 2:
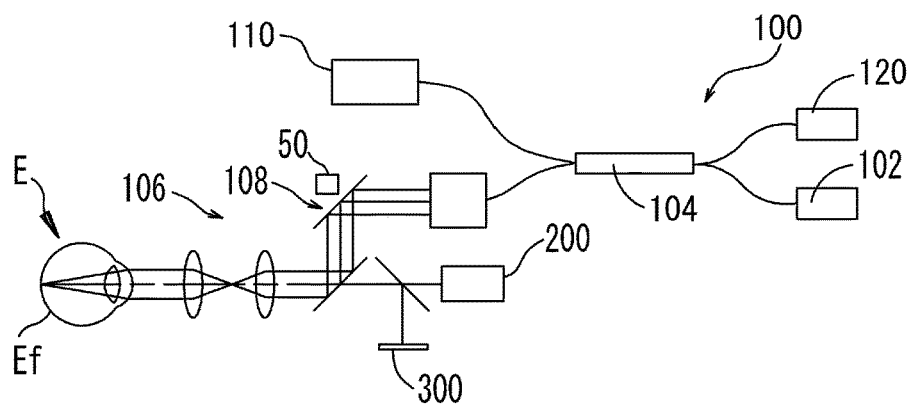
FIG. 2 is a diagram showing the outline of an optical system.

Next, the OCT optical system 100 will be described referring to FIG. 2. The OCT optical system 100 irradiates the fundus with measurement light. The OCT optical system 100 detects an interference state of measurement light reflected by the fundus and reference light by a light receiving element (detector 120). The OCT optical system 100 includes an irradiation position change unit (for example, an optical scanner 108 and a fixation target projection unit 300) which changes an irradiation position of measurement light on the fundus Ef so as to change an imaging position on the fundus Ef. The control unit 70 controls the operation of the irradiation position change unit based on set imaging position information and acquires a tomographic image based on a light reception signal from the detector 120.

<OCT Optical System>

The OCT optical system 100 has the device configuration of a so-called optical tomography interferometer (OCT: Optical coherence tomography) for ophthalmology, and images the tomographic image of the eye E. The OCT optical system 100 splits light emitted from a measurement light source 102 into measurement light (sample light) and reference light by a coupler (light splitter) 104. The OCT optical system 100 guides measurement light to the fundus Ef of the eye E by a measurement optical system 106 and guides reference light to a reference optical system 110. The OCT optical system 100 allows the detector (light receiving element) 120 to receive interference light by synthesis of measurement light reflected by the fundus Ef and reference light.

The detector 120 detects an interference signal of measurement light and reference light. In case of Fourier domain OCT, speckle intensity (speckle interference signal) of interference light is detected by the detector 120, and a complex OCT signal is acquired by Fourier transform of speckle intensity data. For example, the absolute value of the amplitude in the complex OCT signal is calculated to acquire a depth profile (A-scan signal) in a predetermined range. A luminance profile in the depth direction at each scan position of measurement light scanned by the optical scanner 108 is arranged to acquire OCT image data (tomographic image data). The luminance profile in OCT image data is a numerical sequence of the luminance values of the pixels in the depth direction in an A-scan line, and is a graph of a luminance value to the depth direction.

Measurement light may be scanned in a two-dimensional manner to acquire OCT three-dimensional data. An OCT en-face image (for example, an integrated image integrated with respect to the depth direction) may be acquired from OCT three-dimensional data.

A functional OCT signal may be acquired by analysis processing of the complex OCT signal. The functional OCT signal (motion contrast data) at each scan position of measurement light scanned by the optical scanner 108 is arranged to acquire functional OCT image data (motion contrast image data). Measurement light may be scanned in a two-dimensional manner to acquire three-dimensional functional OCT image data (three-dimensional motion contrast data). An OCT functional en-face image (for example, a Doppler en-face image or a speckle variance en-face image) may be acquired from three-dimensional functional OCT image data.

For example, Spectral-domain OCT (SD-OCT) or Swept-source OCT (SS-OCT) is used. Time-domain OCT (TD-OCT) may also be used.

In case of SD-OCT, a low-coherent light source (wideband light source) is used as the light source 102, and the detector 120 is provided with a spectral optical system (spectrometer) which spectrally separates interference light into respective frequency components (respective wavelength components). The spectrometer has, for example, a diffraction grating and a line sensor.

In case of SS-OCT, a wavelength scanning light source (wavelength variable light source) which temporally changes an emission wavelength at high speed is used as the light source 102, and for example, a single light receiving element is provided as the detector 120. The light source 102 has, for example, a light source, a fiber ring resonator, and a wavelength selection filter. For example, a combination of a diffraction grating and a polygon mirror or a filter using a Fabry-Perot etalon is used as the wavelength selection filter.

Light emitted from the light source 102 is split into a measurement light beam and a reference light beam by the coupler 104. The measurement light beam passes through an optical fiber and is then emitted to the air. The light beam is condensed on the fundus Ef through other optical members of the optical scanner 108 and the measurement optical system 106. Light reflected by the fundus Ef is returned to the optical fiber through the same optical path.

The optical scanner 108 scans measurement light on the fundus in a two-dimensional manner (in the XY direction (transverse direction)). The optical scanner 108 is disposed at a position substantially conjugate to a pupil. The optical scanner 108 is, for example, a two galvanomirrors, and the reflection angle thereof is arbitrarily adjusted by a driving mechanism 50.

With this, a light beam emitted from the light source 102 is changed in the reflection (traveling) direction and is scanned on the fundus Ef in an arbitrary direction. With this, the imaging position on the fundus Ef is changed. As the optical scanner 108, a configuration in which light is polarized may be made. For example, other than a reflection mirror (a galvanomirror, a polygon mirror, or a resonant scanner), an acoustic optical element (AOM) which changes the traveling (deflection) direction of light, or the like is used.

The reference optical system 110 generates reference light which is synthesized with reflected light acquired by reflection of measurement light on the fundus Ef. The reference optical system 110 may be of a Michelson type or a Mach-Zehnder type. The reference optical system 110 is formed of a reflection optical system (for example, a reference mirror), and light from the coupler 104 is reflected by the reflection optical system, is returned to the coupler 104 again, and is guided to the detector 120. As another example, the reference optical system 110 is formed of a transmission optical system (for example, an optical fiber), and light from the coupler 104 is transmitted through the transmission optical system without being returned to the coupler 104 and is guided to the detector 120.

The reference optical system 110 has a configuration in which an optical member in a reference light path is moved to change an optical path length difference of measurement light and reference light. For example, the reference mirror is moved in an optical axis direction. A configuration for changing the optical path length difference may be disposed in the measurement light path of the measurement optical system 106.

<En-Face Observation Optical System>

An en-face observation optical system 200 is provided so as to obtain an en-face image of the fundus Ef. The en-face observation optical system 200 includes, for example, an optical scanner which scans measurement light (for example, infrared light) emitted from the light source on the fundus in a two-dimensional manner, and a second light receiving element which receives fundus reflected light through a confocal opening disposed at a position substantially conjugate to the fundus, and has the device configuration of a so-called scanning laser ophthalmoscope (SLO).

As the configuration of the en-face observation optical system 200, a so-called fundus camera type configuration may be used. The OCT optical system 100 may be also used as the en-face observation optical system 200. That is, the en-face image may be acquired using data which forms the tomographic image obtained in the two-dimensional manner (for example, an integrated image in a depth direction of a three-dimensional tomographic image, an integrated value of spectrum data at each XY position, luminance data at each XY position in a given depth direction, a retinal surface image, or the like).

<Fixation Target Projection Unit>

The fixation target projection unit 300 has an optical system for guiding a visual line direction of the eye E. The fixation target projection unit 300 has a fixation target which is presented to the eye E, and can guide the eye E in a plurality of directions.

For example, the fixation target projection unit 300 has a visible light source which emits visible light, and changes a presentation position of a visual target in a two-dimensional manner. With this, the visual line direction is changed, and as a result, an imaging region is changed. For example, if the fixation target is presented from the same direction as the imaging optical axis, the center part of the fundus is set as an imaging region. If the fixation target is presented upward with respect to the imaging optical axis, an upper part of the fundus is set as an imaging region. That is, an imaging region is changed according to the position of the visual target with respect to the imaging optical axis.

As the fixation target projection unit 300, for example, various configurations, such as a configuration in which a fixation position is adjusted by the turning-on positions of LEDs arranged in a matrix and a configuration in which light from a light source is scanned using an optical scanner and a fixation position is adjusted by turning-on control of the light source, are considered. The fixation target projection unit 300 may be of an internal fixation lamp type or an external fixation lamp type.

<Control Unit>

The control unit 70 includes a CPU (processor), a RAM, a ROM, and the like. The CPU of the control unit 70 performs control of the entire device (OCT device 1, OCT optical system 100), for example, the members of the respective configurations. The RAM temporarily stores various kinds of information. The ROM of the control unit 70 stores various programs for controlling the operation of the entire device, initial values, and the like. The control unit 70 may have a plurality of control units (that is, a plurality of processors).

A nonvolatile memory (storage unit) 72, an operating unit (control part) 76, a display unit (monitor) 75, and the like are electrically connected to the control unit 70. The nonvolatile memory (memory) 72 is a non-transitory storage medium which can hold the stored contents even if power supply is shut off. For example, a hard disk drive, a flash ROM, the OCT device 1, a USB memory which is detachably mounted in the OCT optical system 100, or the like can be used as the nonvolatile memory 72. The memory 72 store an imaging control program for controlling imaging of an en-face image and a tomographic image by the OCT optical system 100. The memory 72 stores a signal processing program which enables signal processing of an OCT signal obtained by the OCT device 1. The memory 72 stores various kinds of information regarding imaging, such as a tomographic image (OCT data) in a scan line, a three-dimensional tomographic image (three-dimensional OCT data), a fundus en-face image, and information of an imaging position of a tomographic image. Various operation instructions by an examiner are input to the operating unit 76.

The operating unit 76 outputs a signal according to an input operation instruction to the control unit 70. As the operating unit 76, for example, at least one of a mouse, a joystick, a keyboard, a touch panel, and the like may be used.

The monitor 75 may be a display which is mounted in the device main body, or may be a display connected to the main body. A display of a personal computer (hereinafter, referred to as "PC") may be used. A plurality of displays may be used together. The monitor 75 may be a touch panel. When the monitor 75 is a touch panel, the monitor 75 functions as an operating unit. Various images including a tomographic image and an en-face image imaged by the OCT optical system 100 are displayed on the monitor 75.

<Operation Method, Control Operation>

Figure 3:
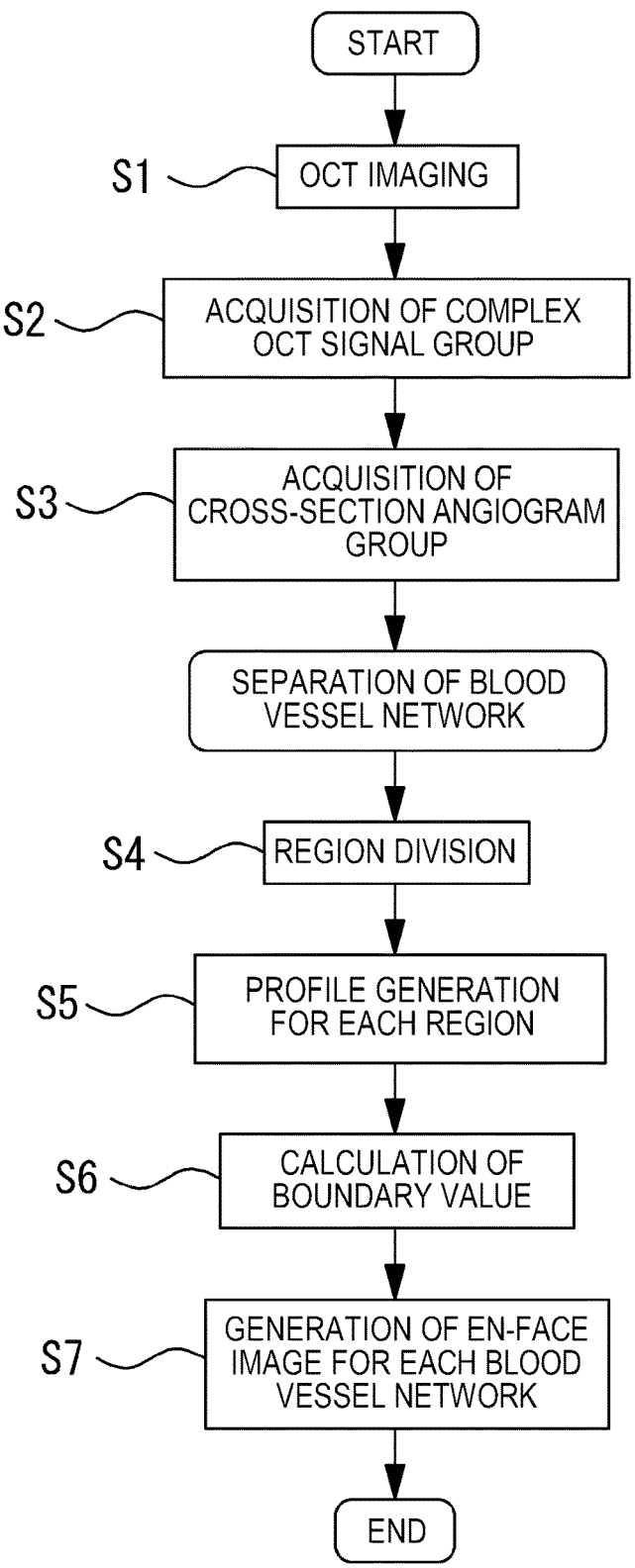
FIG. 3 is a flowchart illustrating processing of this example.

In the present apparatus 10, a tomographic image is acquired. Hereinafter, an operation method and a control operation of the present apparatus 10 will be described referring to FIG. 3. The control unit 70 includes, for example, a processor (for example, a CPU) which performs various kinds of control processing, and a storage medium which stores a program. The processor executes the following processing according to the program. In the following description, although numerals for identifying respective steps of control are assigned, the order of the assigned numerals does not necessarily match the order of actual control.

First, the examiner instructs the subject to keep an eye on the fixation target of the fixation target projection unit 300 and then performs an alignment operation using the operating unit 76 (for example, a joystick (not shown)) while viewing an anterior observation image imaged by a camera for anterior observation on the monitor 75 such that the measurement optical axis is at the center of the pupil of the subject's eye.

(Step 1: OCT Imaging)

Figure 4:
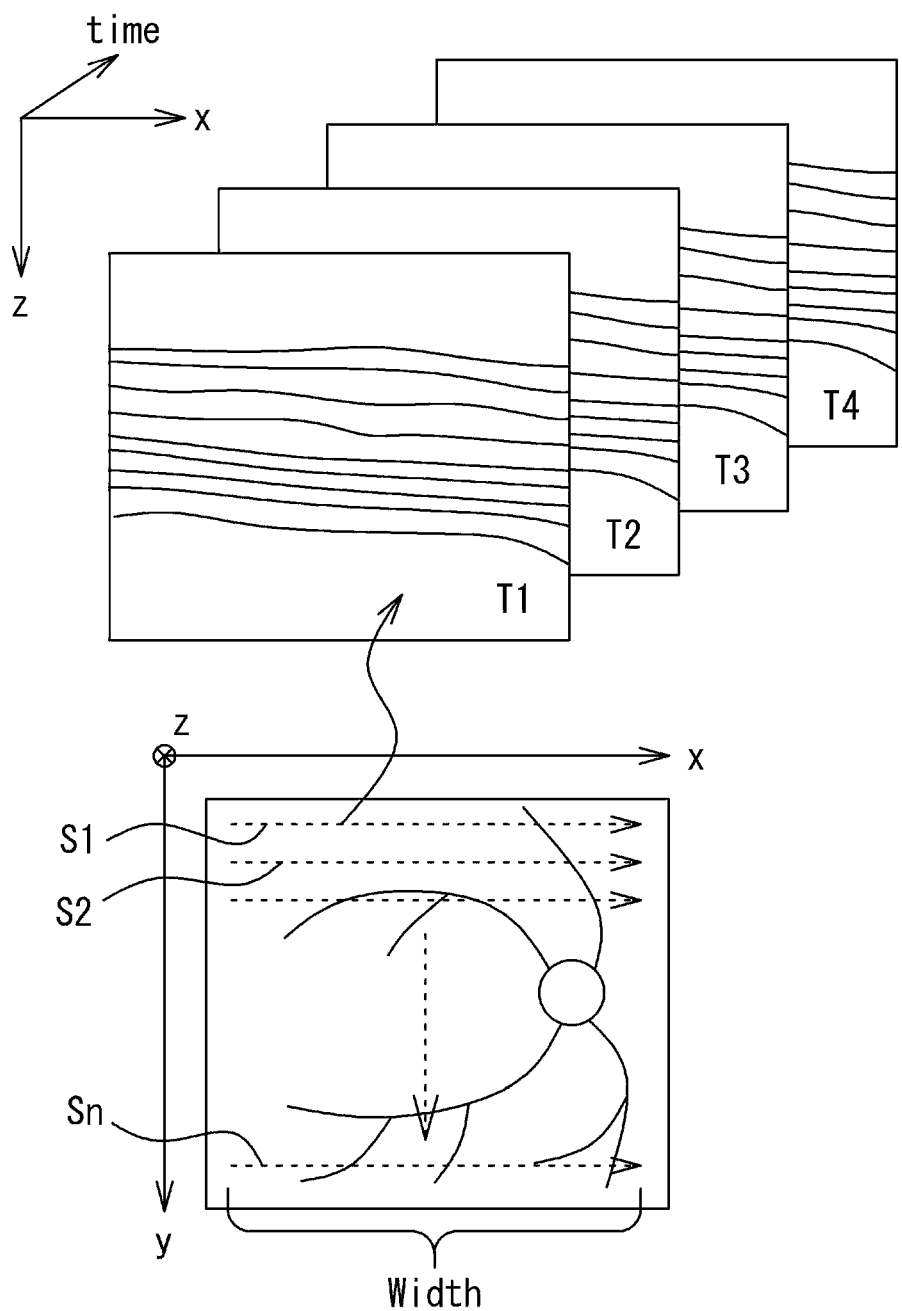
FIG. 4 is an image diagram of a fundus illustrating a measurement of this example.

The control unit 70 acquires interference signals of at least two frames which are temporally different from each other at the same position. For example, the control unit 70 controls the driving of the optical scanner 108 and scans measurement light on the fundus. For example, measurement light is scanned in the x direction along a first scan line S1 shown in FIG. 4. Scan of measurement light in the transverse direction (for example, the x direction) is referred as "B-scan". Hereinafter, an interference signal of one frame will be described as an interference signal obtained by single B-Scan. The control unit 70 acquires an interference signal detected by the detector 120 during the scan. In FIG. 4, the direction of the z axis is referred to as the direction of the optical axis of measurement light. The direction of the x axis is referred to as a direction perpendicular to the z axis and a direction of right and left. The direction of the y axis is referred to as a direction perpendicular to the z axis and a direction of up and down.

If the first scan is completed, the control unit 70 performs second scan at the same position as the first scan. For example, the control unit 70 scans measurement light along the scan line S1 shown in FIG. 4 and then scans measurement light again. The control unit 70 acquires an interference signal detected by the detector 120 during the second scan. Hereby, the control unit 70 can acquire interference signals of two frames which are temporally different from each other at the same position. In this example, scan at the same position is repeated four times, and interference signals of four continuous frames which are temporally different from each other are acquired. For example, scan in the scan line S1 is repeated four times, and interference signals of four frames are acquired.

When interference signals which are temporally different from each other at the same position can be acquired by single scan, the second scan may not be performed. For example, when two beams of measurement light with deviation in optical axis at a predetermined interval are scanned at one time, it is not necessary to perform scan multiple times. It should suffice that interference signals which are temporally different from each other at the same position in the subject can be acquired. When two beams of measurement light are scanned at one time, it is possible to detect an arbitrary blood flow rate as an objective at the interval of the two beams of measurement light.

Similarly, the control unit 70 may acquire signals of at least two frames which are temporally different from each other at another position. As shown in FIG. 4, a first scan line S1 is, for example, y=y1. A second scan line S2 is, for example, y=y2. If the acquisition of signals which are temporally different from each other in the first scan line S1 is completed, the control unit 70 may successively acquire signals of at least two frames which are temporally different from each other in the second scan line S2.

In this way, the control unit 70 acquires signals at different times of the subject. For example, in this example, scan is repeated four times in the same line, and interference signals of four frames are acquired. However, the number of frames is not limited to four frames, and it should suffice that interference signals of at least two frames which are temporally different from each other are acquired.

As shown in FIG. 4, the control unit 70 raster-scans measurement light and obtains interference signals of at least two frames which are temporally different from each other in each scan line. Hereby, it is possible to acquire information three-dimensional information inside a fundus.

Raster scan is a pattern in which measurement light is scanned on a fundus in a rectangular shape. Raster scan is used as, for example, en-face image scan.

In raster scan, for example, measurement light is rasterized in a scan region (for example, a rectangular region) set in advance. As a result, a tomographic image in each scan line in the scan region (for example, a rectangular region) is acquired.

As the scan conditions in raster scan, for example, a line width (the distance between a start point and an end point) in each of a main scan direction and a sub scan direction, a scan rate, the interval between the scan lines, the number of scan lines, and the like are set in advance. Of course, a configuration in which the scan conditions in raster scan are arbitrarily set may be made.

Specifically, the control unit 70 scans measurement light in the main scan direction in a scan line (each line) set as a start position, whereby an interference signal along the main scan direction is acquired. Next, the control unit 70 scans measurement light in the man scan direction in different scan lines with respect to the sub scan direction, whereby interference signals along the main scan direction are acquired. As described above, interference signals are respectively acquired with respect to N lines different from each other. Each scan interval with respect to the sub scan direction is made close, whereby an interference signal can be acquired in a scan region. A scan region is formed by different scan lines with respect to the sub scan direction.

In the following description, although a case where the sub scan direction is set as the y direction (up and down) and the main scan direction is set as the x direction (right and left) has been described, the invention is not limited thereto. For example, the sub scan direction may be the x direction and the main scan direction may be the y direction.

In scan control in the sub scan direction, the scan position may be changed in order from the top to the bottom, or the scan position may be changed in order from the bottom to the top. The scan position may be changed in order from the center to the periphery. As raster scan, an interlace system may be used.

When acquiring interference signals which are temporally different from each other at the same position, for example, the control unit 70 scans measurement light in the first scan line S1 multiple times in the main scan direction. That is, after initial scan from the start position to the end position in the first scan line S1 ends, the control unit 70 returns the scan position of measurement light to the start position in the first scan line S1 again and performs scan in the first scan line S1 again.

The control unit 70 may control the OCT optical system 100 to acquire an interference signal and may control the en-face observation optical system 200 to acquire a fundus en-face image.

(Step 2: Acquisition of Complex OCT Signal Group)

Subsequently, the control unit 70 processes the interference signals acquired by the OCT optical system 100 and acquires complex OCT signals. For example, the control unit 70 performs Fourier transform of the interference signals acquired in Step 1. Here, a signal at an (x, z) position of an n-th frame among N frames is expressed by An(x, z). The control unit 70 obtains a complex OCT signal An(x, z) by Fourier transform. The complex OCT signal An(x, z) includes a real component and an imaginary component.

The control unit 70 may perform image positioning (image registration), phase correction, or the like. Image registration is, for example, processing for arranging a plurality of images of the same scene. As a factor of positional shift of images, for example, the motion of the subject's eye during imaging is considered. Phase correction is, for example, processing for correcting positional shift between A-lines in an image.

(Step 3: Acquisition of Cross-Section Angiogram Group)

Next, the control unit 70 processes the complex OCT signals acquired in Step 2 and acquires a cross-section angiogram group (motion contrast image group). As a method of processing the complex OCT signals, for example, a method of calculating the phase difference of the complex OCT signals, a method of calculating the vector difference of the complex OCT signal, a method of multiplying the phase difference and the vector difference of the complex OCT signals, or the like is considered. In this example, a method of multiplying the phase difference and the vector difference will be described as an example.

First, the control unit 70 calculates a phase difference for complex OCT signals A(x, z) acquired at two or more different times at the same position. The control unit 70 calculates a temporal change in phase, for example, using Expression (1). In this example, for example, since a measurement is performed at four different times, three calculations in total of T1 and T2, T2 and T3, and T3 and T4 are performed, and three pieces of data are calculated. In the numerical expression, An represents a signal acquired at the time Tn, and * represents a complex conjugate.

[Equation 1]

$$\Delta\phi_n(x,z) = \arg(A_{n+1}(x,z) \times A_n^*(x,z)) \quad (1)$$

The control unit 70 adds and averages signals of three frames and removes noise. Since a noise component is present in each frame randomly, the noise component becomes smaller than a signal component by addition-averaging. The control unit 70 performs the addition-averaging processing, for example, using Expression (2).

[Equation 2]

$$|\Delta\phi(x, z)| = \frac{1}{N-1} \sum_{n=1}^{N-1} |\Delta\phi_n(x, z)| \quad (2)$$

Subsequently, the control unit 70 calculates the vector difference of the complex OCT signals. For example, the vector difference of the complex OCT signals detected by the OCT optical system is calculated. For example, a complex OCT signal can be expressed as a vector on a complex plane. Accordingly, signals A1 and A2 at the same position are detected at certain times T1 and T2, and a vector difference ΔA is calculated by Expression (3) to generate motion contrast data. In this example, for example, since a measurement is performed at four different times, three calculations in total of T1 and T2, T2 and T3, and T3 and T4 are performed, and three pieces of data are calculated. When imaging the vector difference ΔA, for example, imaging may be performed based on phase information, other than the magnitude of the difference ΔA.

[Equation 3]

$$|\Delta A_n(x,z)| = |A_{n+1}(x,z) - A_n(x,z)| \quad (3)$$

The control unit 70 adds and averages signals for three frames and removes noise. The control unit 70 performs the addition-averaging processing of the vector difference, for example, using Expression (4).

[Equation 4]

$$|\Delta A(x, z)| = \frac{1}{N-1} \sum_{n=1}^{N-1} |\Delta A_n(x, z)| \quad (4)$$

If the vector difference and the phase difference are calculated, the control unit 70 uses the calculation result of the phase difference to the vector difference as a filter. In the description of this example, "filter application" performs, for example, weighting to a certain numerical value. For example, the control unit 70 performs weighting by multiplying the calculation result of the phase difference to the calculation result of the vector difference. That is, the vector difference of a portion with a small phase difference is weakened, and the vector difference of a portion with a large phase difference is strengthened. Hereby, the calculation result of the vector difference is weighted by the calculation result of the phase difference.

The control unit 70 multiplies, for example, the calculation result of the vector difference and the calculation result of the phase difference. For example, the control unit 70 multiplies the calculation result of the vector difference and the calculation result of the phase difference using Expression (5). Hereby, the control unit 70 generates a cross-section angiogram (CA) weighted by the calculation result of the phase difference.

[Equation 5]

$$CA(x,z) = |\Delta\phi(x,z)| \times |\Delta A(x,z)| \quad (5)$$

It is possible to cancel a disadvantage of each measurement method by multiplying the calculation result of the vector difference and the calculation result of the phase difference, and to detect an image of a blood vessel part well.

Figure 5:
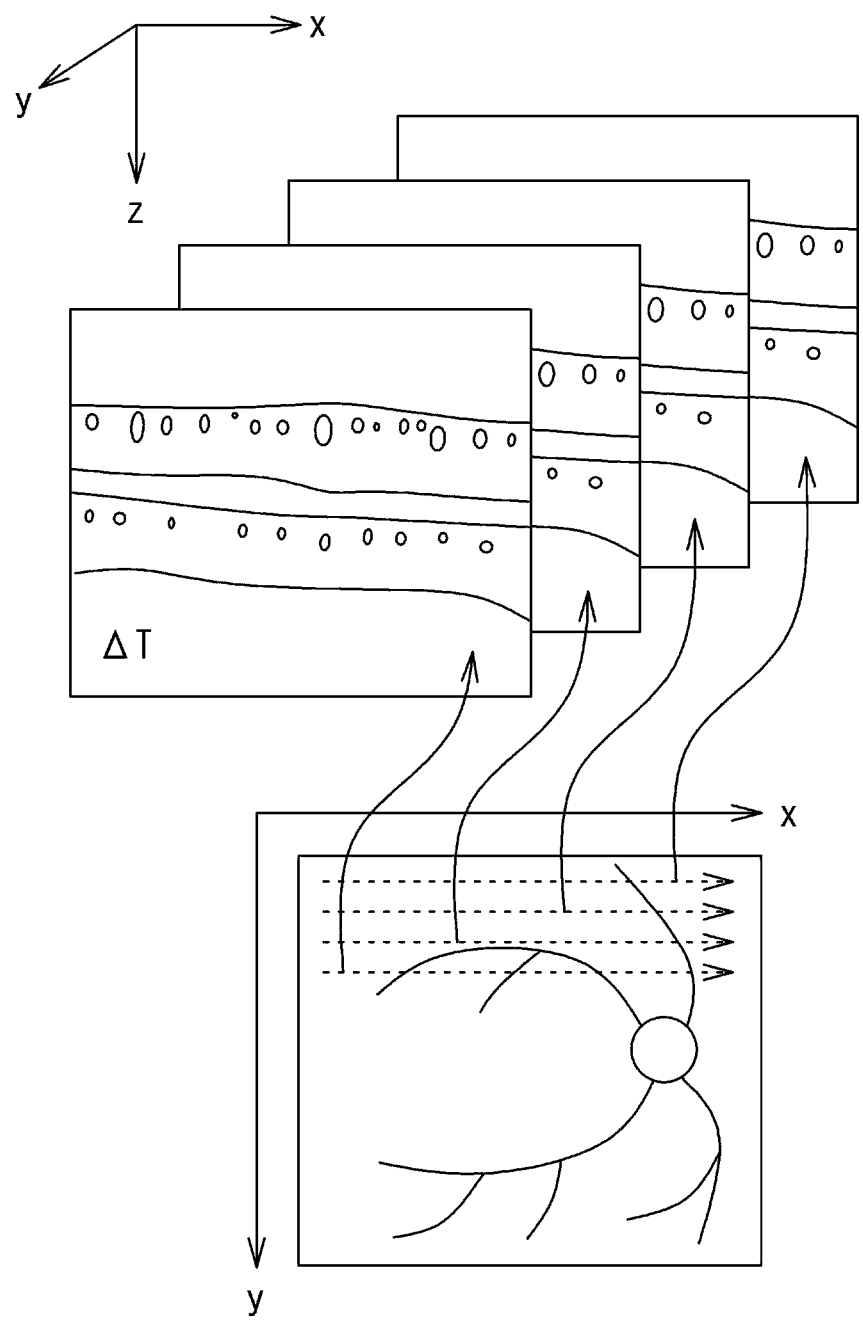
FIG. 5 is an image diagram showing a cross-section angiogram.

The control unit 70 repeats the processing described above for each scan line, and as shown in FIG. 5, generates a cross-section angiogram for each scan line.

<Separation of Blood Vessel Network>

Subsequently, separation of a blood vessel network will be described. A blood vessel network represents a capillary which runs in the form of mesh when viewed from the front direction. Here, a blood vessel network in a fundus has a plurality of layer structures in the depth direction, and a depth position of each blood vessel network is caused by a position of a specific retinal layer, a lesion, and the like.

(Step 4: Region Division)

First, the control unit 70 divides a blood vessel volume image, which is an aggregate of two-dimensional blood vessel images, into a plurality of regions on an XY plane. In subsequent steps, a blood vessel network is separated for each divided region. Hereby, even when the distribution of a blood vessel is locally different due to a disease or the like, it is possible to appropriately separate a blood vessel network by detecting other blood vessels in the region.

There is a possibility that the position or distribution of a blood vessel has variation even in the same blood vessel network. For this reason, a blood vessel network is separated for each region in a certain range, whereby it is possible to reduce variation in a depth of a blood vessel network for each pixel.

A blood vessel network is separated for each region in a certain range, whereby it is possible to cope with the absence of a blood vessel.

It is possible to reduce the processing time by analyzing a luminance profile integrated for each region compared to a case of analyzing a luminance profile for each pixel.

As one of division methods, for example, in FIG. 6A, a method of dividing a region of an image in a square lattice form is considered. In an example of FIG. 6A, a blood vessel volume image is divided into 8×8=64 divisions. An n-th row and m-th column region is expressed by Gnm. In an example of FIG. 6B, a region is divided concentrically. Since a concentric structure is made around the fovea, a region may be divided concentrically, and separation of a blood vessel network conforming to a structure of an eye is performed. The magnitude and shape of a region to be divided may be freely set. For example, the invention is not limited to the examples of FIGS. 6A and 6B, and a triangular shape or other polygonal shapes may be used, or an elliptical shape may be used. For example, it is preferable that the magnitude of each region is at least equal to or greater than a blood vessel interval (for example, 50 μm) such that a plurality of blood vessels are within a region.

(Step 5: Profile Generation for Each Region)

Figure 7:
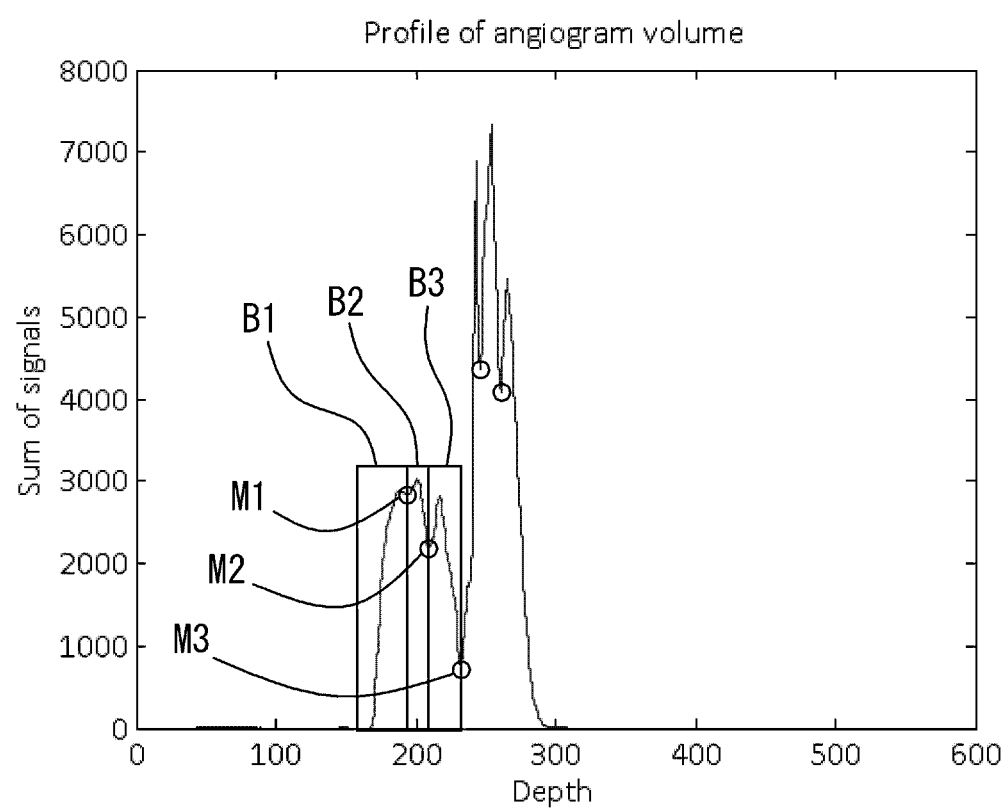
FIG. 7 is a graph showing a luminance profile in a depth direction.

Subsequently, the control unit 70 obtains a luminance profile (luminance distribution) in the depth direction of motion contrast for each region divided in Step 4. For example, a luminance profile in the depth direction at each XY pixel inside a region G11 of FIG. 6A is added with respect to the XY direction. That is, a luminance value corresponding to the same depth position in each luminance profile included in the divided region is added, and as a result, a luminance profile obtained by adding the luminance profile in the depth direction at each XY pixel is created. Next, the control unit plots the added luminance profile for each depth. For example, the luminance profile in the depth direction in the region G11 can be expressed in a graph shown in FIG. 7. In the graph of FIG. 7, the vertical axis represents a luminance value, and the horizontal axis represents a depth.

(Step 6: Calculation of Boundary Value)

Subsequently, the control unit 70 calculates a depth, which becomes a boundary of a blood vessel network, from the luminance profile generated in Step 5. As a method of calculating a boundary value of a blood vessel network, for example, a method of searching for a local minimum value of a luminance profile is considered. A place where a profile of a luminance value becomes local minimum is a place where motion contrast is small, that is, a place where there are few blood vessels. For example, the control unit 70 calculates the inclination of the graph of the luminance profile and searches a point where the inclination changes from negative to positive as a place where the profile becomes local minimum.

The control unit 70 separates the blood vessel network based on the calculated boundary value. For example, the control unit 70 separates the blood vessel network with the local minimum value of the luminance profile as the boundary. In many cases, there are few blood vessels near the boundary of the blood vessel network. Accordingly, the blood vessel network is separated with a place where the luminance value is locally small, that is, a place where there are few blood vessels. For example, as shown in FIG. 7, the blood vessel network may be separated such that a layer to a local minimum value M1 at the shallowest position from the surface of the retina is referred to as a first layer (first blood vessel network) B1, a layer from the local minimum value M1 to a subsequent local minimum value M2 is referred to as a second layer (second blood vessel network) B2, and a layer from the local minimum value M2 to a local minimum value M3 is referred to as a third layer (third blood vessel network) B3. In this example, the first layer B1 corresponds to a superficial capillary plexus (SCP), the second layer B2 corresponds to an intermediate capillary plexus (ICP), and the third layer B3 corresponds to a deep capillary plexus (DCP).

In this example, although a case where the blood vessel network is separated into three layers has been described, the blood vessel network may be separated into two layers or may be separated into three or more layers.

(Step 7: En-Face Image Generation)

Figure 8A:
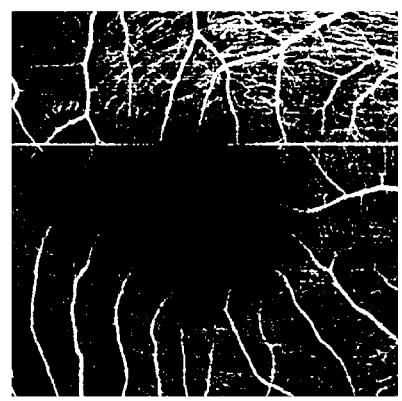
FIGS. 8A to 8C show an example of an en-face angiogram generated for each layer.
Figure 8B:
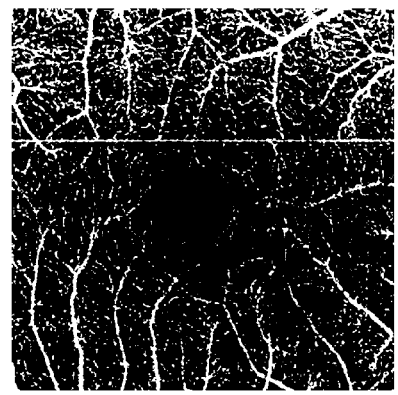
Figure 8C:
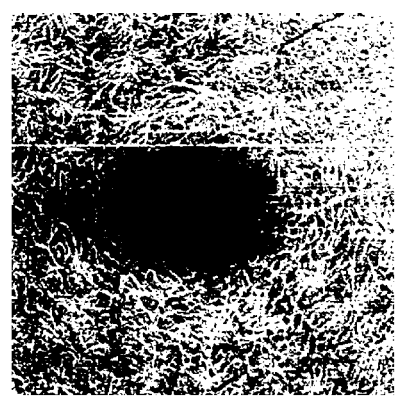

Subsequently, the control unit 70 acquires an en-face angiogram for each blood vessel network separated in Step 6. For example, the control unit 70 integrates an image at a depth corresponding to each layer of the three-layered blood vessel network of the three layers separated in Step 6 in the z direction to generate an angiogram. The control unit 70 performs the above-described processing to generate an angiogram shown in FIGS. 8A to 8C. FIGS. 8A to 8C show an example of an en-face angiogram generated for each layer. FIG. 8A shows an example of an angiogram generated in the first layer B1. FIG. 8B shows an example of an angiogram generated in the second layer B2. FIG. 8C shows an example of an angiogram generated in the third layer B3. The control unit 70 may display the generated images on the display unit or may transfer the generated images to other devices.

Although a position where a blood vessel is present can be estimated anatomically, there is a case where a blood vessel is present at a position, at which a blood vessel is not present originally, due to a disease or the like. For this reason, when an en-face angiogram is dividedly generated for each region estimated anatomically, as described above, there is a possibility that a blood vessel which is present at a position deviated from a normal position due to a disease or the like is separated from an image.

Accordingly, in this example, a blood vessel network is separated from distribution information obtained by motion contrast, and an angiogram is generated for each separated blood vessel network. Hereby, even a blood vessel which is present at a position deviated from a normal position due to a disease or the like is imaged as a part of a blood vessel network. Therefore, the examiner can observe the state of a disease for each blood vessel network, and a new diagnostic method can be established.

In the above description, although a blood vessel network is separated with a local minimum value of a luminance profile as a boundary, the invention is not limited thereto. For example, a local maximum value of a luminance profile may be searched, and a blood vessel network may be separated using information regarding the local maximum value of the luminance profile. A place where a luminance profile becomes local maximum is a place where motion contrast is large, that is, a place where there are many blood vessels. For example, the control unit 70 calculates the inclination of the graph of the luminance profile and searches a place where the inclination changes from positive to negative as a place where the profile becomes local maximum. For example, a region of about five pixels centering on the searched place may be separated as one blood vessel network.

When separating a blood vessel network, the integration of a spatial frequency when a blood vessel volume image is subjected to two-dimensional Fourier transform may be used. For example, since a high-frequency component increases to a spatial frequency due to the presence of a blood vessel structure, an increase or decrease in luminance of a spatial frequency spectrum is used.

For example, as shown in FIG. 9A, if an en-face angiogram at a certain depth is subjected to Fourier transform, a spatial frequency spectrum shown in FIG. 9B is obtained. If there are many blood vessel structures in an en-face angiogram, a high-frequency component increases in the spatial frequency spectrum after Fourier transform. Accordingly, when a low-frequency component is removed, the integrated value of luminance of the spatial frequency spectrum increases. For example, as shown in FIG. 9C, the luminance profile in the depth direction of the spatial frequency spectrum with the low-frequency component removed changes in the luminance value according to the depth. Therefore, as described above, a depth where the luminance profile of FIG. 9C becomes local minimum or local maximum may be calculated, and a boundary of a blood vessel network may be obtained. When removing a low-frequency component from the spatial frequency spectrum, for example, a high-pass filter may be used. For example, a frequency component equal to or greater than a threshold value may be extracted by the high-pass filter.

Figure 10A:
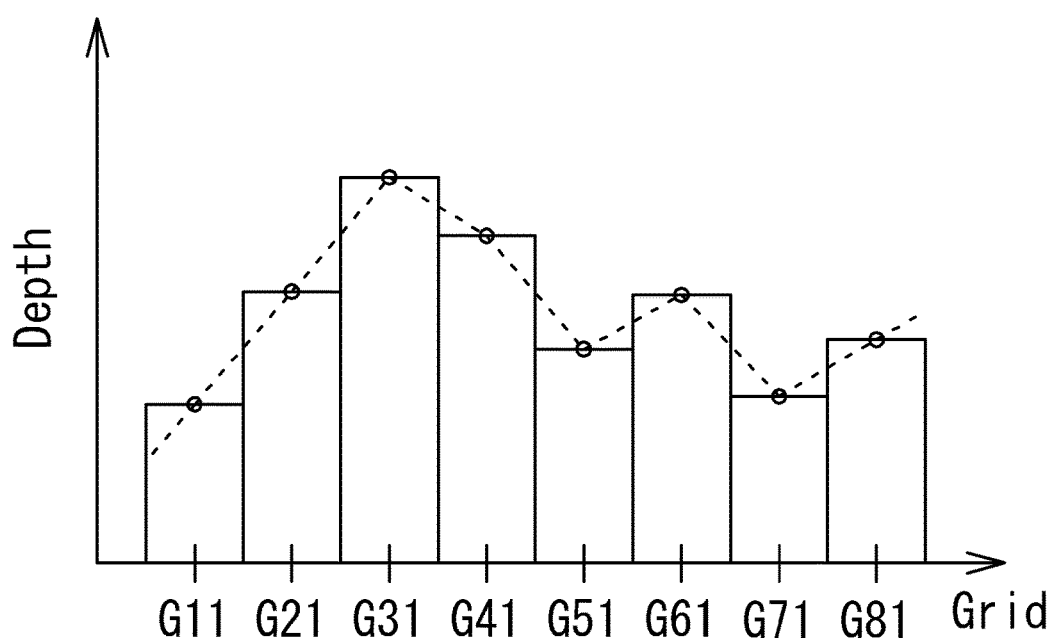
FIGS. 10A and 10B are diagrams illustrating an example of processing when a blood vessel network is separated.
Figure 10B:
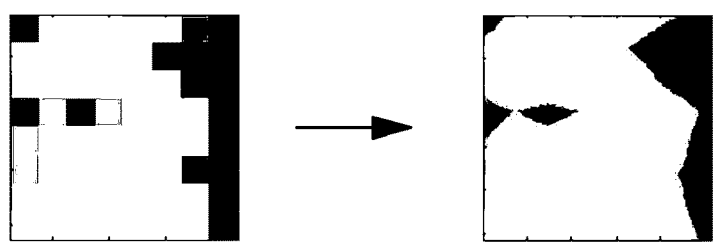

When the depth of each blood vessel network is determined for each region, as in FIG. 10a, a step is formed in a boundary of a region. Accordingly, the numerical value of a depth of each region may be interpolated so as to be close to the shape of an actual blood vessel network. For example, as shown in FIG. 10A, the numerical value of a depth of the blood vessel network may be linearly interpolated based on a central pixel of the region. Hereby, a step of each region is eliminated, and a blood vessel network can be separated to a shape close to an actual one (see FIG. 10B).

Figure 11:
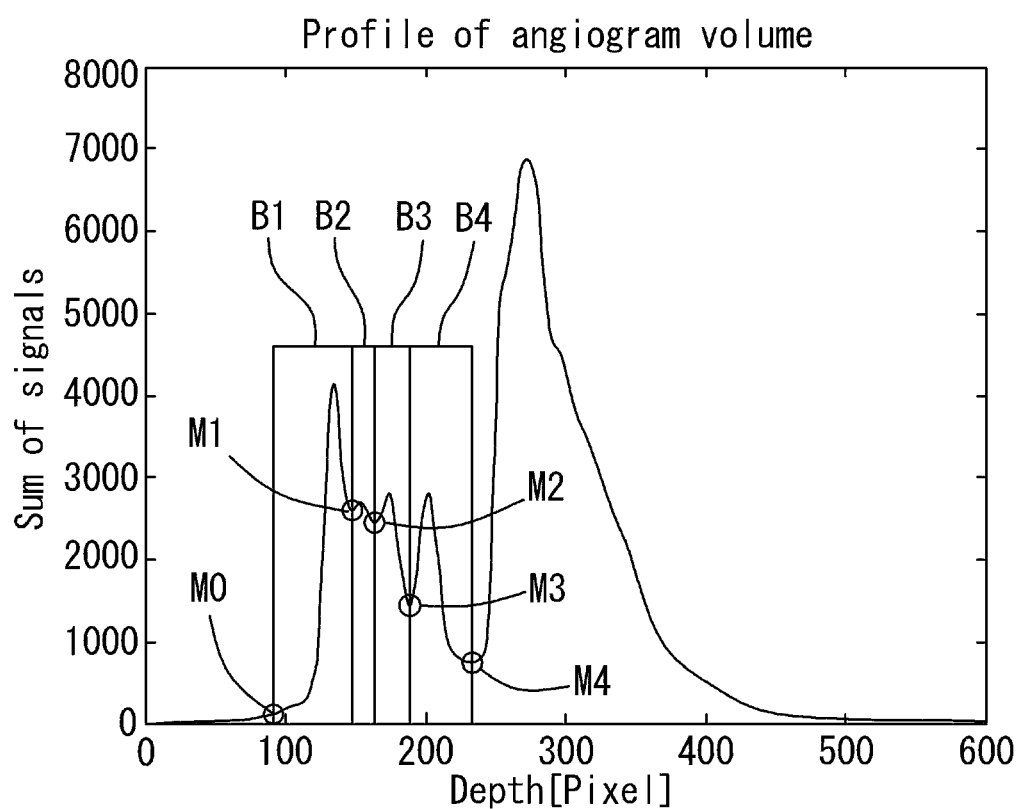
FIG. 11 is a graph showing a luminance profile in a depth direction.

In the above description, as shown in FIG. 7, an example where the control unit 70 separates the blood vessel network from the first layer to the third layer has been described. However, as shown in FIG. 11, the control unit 70 may separate a blood vessel network into a first layer to a fourth layer, or five layers, six layers, seven layers, eight layers, nine layers, ten layers, or more layers. In an example of FIG. 11, a blood vessel network may be separated such that a layer from a local minimum value M0 at the shallowest position from the surface of the retina to a subsequent local minimum value M1 is referred to as a first layer (first blood vessel network) B1, a layer from the local minimum value M1 to a subsequent local minimum value M2 is referred to as a second layer (second blood vessel network) B2, a layer from the local minimum value M2 to a local minimum value M3 is referred to as a third layer (third blood vessel network) B3, and a layer from the local minimum value M3 to a local minimum value M4 is referred to as a fourth layer (fourth blood vessel network) B4. Of course, the control unit 70 may separate a blood vessel network into four or more layers by another boundary value, such as a local maximum value.

Figure 12A:
FIGS. 12A to 12D show an example of an en-face angiogram generated for each layer.
Figure 12B:
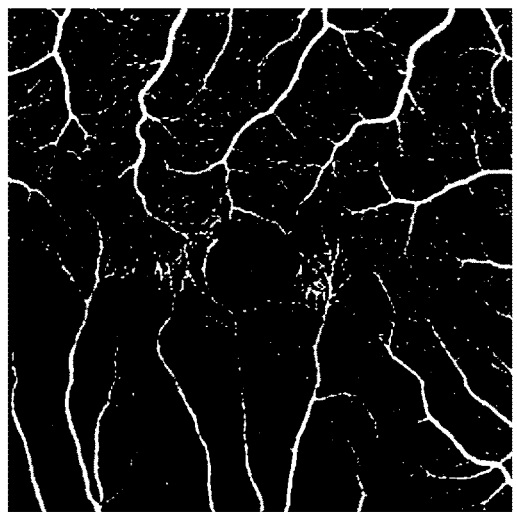
Figure 12C:
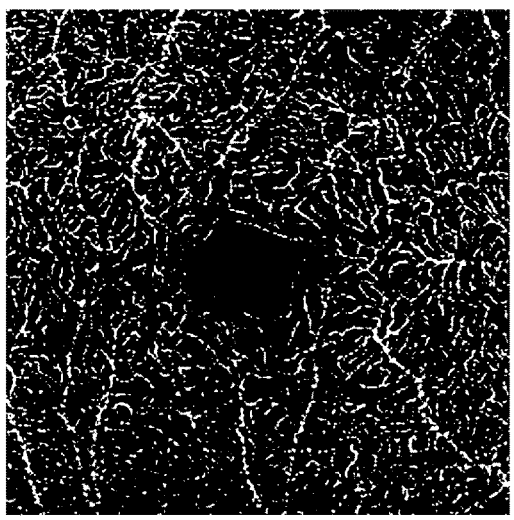
Figure 12D:
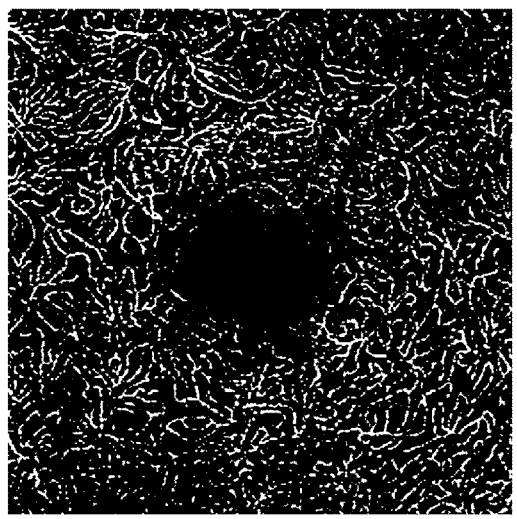

In the example of FIG. 11, the first layer B1 corresponds to a nerve fiber layer (NFL), a second layer B2 corresponds to a superficial capillary plexus (SCP), a third layer B3 corresponds to an intermediate capillary plexus (ICP), and a fourth layer B4 corresponds to a deep capillary plexus (DCP). The first layer B1 may be expressed as a radial peripapillary capillaries (RPC). FIGS. 12A to 12D show an en-face image of each blood vessel network when a blood vessel network is separated into four layers. FIG. 12A shows an en-face image of a blood vessel network in the first layer B1, FIG. 12B shows an en-face image of a blood vessel network in the second layer B2, FIG. 12C shows an en-face image of a blood vessel network in the third layer B3, and FIG. 12D shows an en-face image of a blood vessel network in the fourth layer B4.

As described above, the control unit 70 may detect a change resulting from each of blood vessels at different positions in the depth direction inside the fundus to detect four or more blood vessel networks included in the subject's eye, and may separate each blood vessel network into four or layers in the depth direction based on the detection results.

What is claimed is:
1. An optical coherence tomography apparatus comprising:
   an OCT optical system configured to detect an OCT signal based on measurement light scanned on a plurality of scan positions of a subject including a blood vessel network by a scanning unit and reference light corresponding to the measurement light;
   a processor; and
   a memory storing a computer program, when executed by the processor, causing the optical coherence tomography apparatus to execute:
   a signal processing instruction of processing a plurality of OCT signals which are temporally different from each other with respect to a same position on the subject and generating a motion contrast image which images distribution of a moving object in a depth direction for each of the scan positions based on the plurality of OCT signals; and
   a detecting instruction of analyzing a profile in the depth direction of the motion contrast image generated by the signal processing unit and detecting a change resulting from a blood vessel of the blood vessel network to detect the blood vessel network included in the subject,
   wherein the detecting instruction causes the optical coherence tomography apparatus to detect a change resulting from the blood vessels at different positions in the depth direction to detect a plurality of the blood vessel networks, and separate the blood vessel networks into each of the blood vessel networks in the depth direction based on detection results, and
   wherein the change comprises at least one of a local minimum or a local maximum of a spatial frequency spectrum of the OCT signals.

2. The optical coherence tomography apparatus according to claim 1, wherein the subject is an eye, and
   the OCT optical system detects the OCT signal based on measurement light scanned on the plurality of scan positions of the fundus of the eye.

3. The optical coherence tomography apparatus according to claim 1,
   wherein the detecting instruction causes the optical coherence tomography apparatus to analyze a luminance profile in the depth direction and detect a change in luminance resulting from the blood vessel to detect the blood vessel network included in the subject.

4. The optical coherence tomography apparatus according to claim 1,
   wherein the detecting instruction causes the optical coherence tomography apparatus to analyze a luminance profile of the spatial frequency spectrum in the depth direction and detects a change in luminance resulting from the blood vessel to detect a blood vessel network included in the subject, the spatial frequency spectrum being obtained by two-dimensional Fourier transform of the motion contrast image.

5. The optical coherence tomography apparatus according to claim 1,
   wherein the detecting instruction causes the optical coherence tomography apparatus to detect, as a boundary of the blood vessel network, a depth where the profile has the at least one of the local minimum or the local maximum.

6. The optical coherence tomography apparatus according to claim 1, wherein
   the OCT optical system is configured to acquire the plurality of OCT signals at each scan position in a two-dimensional manner by two-dimensionally scanning the measurement light on the subject,
   the signal processing instruction causes the optical coherence tomography apparatus to generate three-dimensional motion contrast data as an aggregate of motion contrast images having different transverse positions based on the plurality of OCT signals acquired in the two-dimensional manner, and the detecting instruction causes the optical coherence tomography apparatus to detect the blood vessel network in each of the motion contrast images to two-dimensionally detect the blood vessel network in the three-dimensional motion contrast data.

7. The optical coherence tomography apparatus according to claim 6, wherein
the computer program when executed by the processor causes the optical coherence tomography apparatus to further execute:
an en-face image generation instruction of generating an en-face image obtained by visualizing the motion contrast images in a front direction based on the profile in the depth direction in the blood vessel network detected by the detecting instruction.

8. The optical coherence tomography apparatus according to claim 7, wherein
the detecting instruction causes the optical coherence tomography apparatus to detect the change resulting from the blood vessels at different positions in the depth direction by analyzing the profile to detect the plurality of the blood vessel networks included in the subject, and to separate the blood vessel networks in the depth direction based on the detection results of the change resulting from the blood vessels at different positions in the depth direction, and
the en-face image generation instruction causes the optical coherence tomography apparatus to generate an en-face image corresponding to each of the blood vessel networks based on a profile in the depth direction in each of the blood vessel networks separated by the detecting instruction.

9. The optical coherence tomography apparatus according to claim 6,
wherein the detecting instruction causes the optical coherence tomography apparatus to divide the three-dimensional motion contrast data into a plurality of small regions with respect to the front direction, analyze the profile in the divided small regions, and detect the change resulting from the blood vessel in each of the small regions to detect a blood vessel network included in the subject.

10. A non-transitory computer readable recording medium storing a data processing program, which is executed by a processor of an optical coherence tomography apparatus including an OCT optical system configured to detect an OCT signal based on measurement light scanned on a plurality of scan positions of a subject including a blood vessel network by a scanning unit and reference light corresponding to the measurement light, the data processing program when executed by the processor of the optical coherence tomography apparatus causing the optical coherence tomography apparatus to execute:
a signal processing instruction of processing a plurality of OCT signals which are temporally different from each other with respect to a same position on the subject and generating a motion contrast image which images distribution of a moving object in a depth direction at each of the scan positions based on the plurality of OCT signals; and
a detecting instruction of analyzing a profile in the depth direction of the motion contrast image generated by the signal processing unit and detecting a change resulting from the blood vessel to detect the blood vessel network included in the subject,
wherein the detecting instruction causes the optical coherence tomography apparatus to detect a change resulting from the blood vessels at different positions in the depth direction to detect a plurality of the blood vessel networks, and separate the blood vessel networks into each of the blood vessel networks in the depth direction based on detection results, and
wherein the change comprises at least one of a local minimum or a local maximum of a spatial frequency spectrum of the OCT signals.

11. The optical coherence tomography apparatus according to claim 1,
wherein the spatial frequency spectrum of the OCT signals comprises an angiogram volume of a sum of the OCT signals with respect to the depth direction.

12. The optical coherence tomography apparatus according to claim 10,
wherein the computer program, when executed by the processor, further causes the optical coherence tomography apparatus to execute generation of the spatial frequency spectrum of the angiogram volume by Fourier transformation and summation of the OCT signals with respect to the depth direction in pixels of the motion contrast image.

13. The optical coherence tomography apparatus according to claim 1,
wherein the blood vessel networks are respective capillaries.

14. An optical coherence tomography apparatus comprising:
an OCT optical system configured to detect an OCT signal based on measurement light scanned on a plurality of scan positions of a subject including a blood vessel network by a scanning unit and reference light corresponding to the measurement light;
a processor; and
a memory storing a computer program, when executed by the processor, causing the optical coherence tomography apparatus to execute:
a signal processing instruction of processing a plurality of OCT signals which are temporally different from each other with respect to a same position on the subject and generating a motion contrast image which images distribution of a moving object in a depth direction for each of the scan positions based on the plurality of OCT signals; and
a detecting instruction of analyzing a profile in the depth direction of the motion contrast image generated by the signal processing unit and detecting a change resulting from a blood vessel of the blood vessel network to detect the blood vessel network included in the subject,
wherein the OCT optical system is configured to acquire the plurality of OCT signals at each scan position in a two-dimensional manner by two-dimensionally scanning the measurement light on the subject,
the signal processing instruction causes the optical coherence tomography apparatus to generate three-dimensional motion contrast data as an aggregate of motion contrast images having different transverse positions based on the plurality of OCT signals acquired in the two-dimensional manner, and the detecting instruction causes the optical coherence tomography apparatus to detect the blood vessel network in each of the motion contrast images to two-dimensionally detect the blood vessel network in the three-dimensional motion contrast data,
wherein the computer program when executed by the processor causes the optical coherence tomography apparatus to further execute:

an en-face image generation instruction of generating an en-face image obtained by visualizing the motion contrast images in a front direction based on the profile in the depth direction in the blood vessel network detected by the detecting instruction, wherein the detecting instruction causes the optical coherence tomography apparatus to detect a change resulting from the blood vessels at different positions in the depth direction by analyzing the profile to detect a plurality of the blood vessel networks included in the subject, and to separate the blood vessel networks in the depth direction based on the detection results of the change resulting from the blood vessels at different positions in the depth direction, and wherein the en-face image generation instruction causes the optical coherence tomography apparatus to generate an en-face image corresponding to each of the blood vessel networks based on a profile in the depth direction in each of the blood vessel networks separated by the detecting instruction.

* * * * *